United States Patent [19]

Konai et al.

[11] Patent Number: 4,614,620
[45] Date of Patent: Sep. 30, 1986

[54] PROCESS FOR PRODUCING I-BRASSICASTEROL

[75] Inventors: Yutaka Konai; Shoichiro Hayashi; Yoshikazu Kubota; Kouichi Kodama, all of Iwaki, Japan

[73] Assignee: Kureha Kagaku Kogyo Kabushiki Kaisha, Tokyo, Japan

[21] Appl. No.: 702,633

[22] Filed: Feb. 19, 1985

[30] Foreign Application Priority Data

Feb. 28, 1984 [JP] Japan .................................. 59-36921

[51] Int. Cl.$^4$ .............................................. C07J 9/00
[52] U.S. Cl. .............................................. 260/397.25
[58] Field of Search .................................... 260/397.25

[56] References Cited

FOREIGN PATENT DOCUMENTS 0013800 1/1985 Japan .............................. 260/397.25

OTHER PUBLICATIONS

Chem. Abs., vol. 63, 10014g (1965).

A. Windaus und A. Welsch, Berichte, vol. 42, pp. 612-616, (1909).
M. Anastasia, P. Ciuffreda, and A. Fiecchi, J. Chem. Soc. Perkin Trans., vol. I, pp. 379-382 (1983).

Primary Examiner—Albert L. Roberts
Attorney, Agent, or Firm—Oblon, Fisher, Spivak, McClelland & Maier

[57] ABSTRACT

Disclosed herein is a process for producing i-brassicasterol, comprising charging a mixture of i-sterols derived from a mixture of sterols including brassicasterol into a column packed with a filler obtained by chemically binding alkyl group(s) of 15 to 24 carbon atoms to silica, and subjecting said mixture of i-sterols to reversed-phase partition column-chromatography while using (i) an alcohol of one to three carbon atoms or a mixture therof, or (ii) a mixed solvent comprising more than 50% by volume of said alcohol(s) and a solvent other than said alcohol(s) as an eluent, thereby isolating and purifying i-brassicasterol.

3 Claims, 6 Drawing Figures

PROCESS FOR PRODUCING I-BRASSICASTEROL

BACKGROUND OF THE INVENTION

The present invention relates to a process for producing i-brassicasterol (chemical name: 3,5-cycloergost-22-en-6β-ol) which is an intermediate for producing the compound showing a phytohormone activity, and more in detail, relates to a process for producing i-brassicasterol comprising converting a mixture of natural sterols including brassicasterol into a mixture of i-sterols, and treating the thus converted mixture by the reversed-phase partition column-chromatography, thereby isolating i-brassicasterol from the mixture of i-sterols and purifying i-brassicasterol.

Recently, from the pollen of Brassica naps L., brassinolide has been found as a substance having a plant growth-promoting activity, and the chemical structure thereof has been identified (refer to Chemical and Engineering News, No. 5, page 20(1979)).

Thereafter, many brassinolide-related compounds including brassinolide itself have been synthesized, and their activity to plants has been examined. As a result, it was reported that the 24R-epimer of brassinolide had a considerable plant growth-promoting activity (refer to Org. Chem., 44, 5002(1979)) and accordingly, an industrial process for producing brassinolides having a high activity to plants has come to be demanded. Since it is necessary to obtain i-brassicasterol as the intermediate for producing the brassinolides, development of the industrially advantageous process for producing i-brassicasterol has come to be expected.

Hitherto, as a process for producing i-brassicasterol, several processes have been known, for instance, a process in which ergosterol (which is easily available as a single substance in a relatively pure state) is used as the starting material and is converted into i-brassicasterol via i-ergosterol, a process in which brassicasterol is prepared from ergosterol and the thus prepared brassicasterol is converted to i-brassicasterol and a process in which brassicasterol is separated from a phytosterol mixture containing brassicasterol and then brassicasterol is converted into i-brassicasterol.

However, in the above-mentioned process in which i-brassicasterol is derived from ergosterol, for instance, a process via i-ergosterol, the following 5 steps are necessary.

(1) tosylation, (2) hydrolysis, (3) oxydation, (4) Birch-reduction and (5) reduction by aluminum-lithium hydride (refer to Steroids 5,745 (1965)). Accordingly, such a process not only takes a long time for obtaining the object compound, i-brassicasterol, but also gives only a low yield. The process has a problem in maintenance due to the use of strongly inflammable reagent such as metallic lithium, and is not practical as an industrial process. So, the process is applicable for the preparation in only laboratory. Then, the process in which i-brassicasterol is derived from ergosterol via brassicasterol is further complicated in the steps of the procedure, and is not practical as an industrial process.

Also, in the process in which brassicasterol is separated from the mixture of phytosterols, the following five steps are necessary for separating brassicasterol itself.

(1) acetylation, (2) bromination, (3) crystallization, (4) de-bromination and (5) hydrolysis, and since the process uses highly corrosive bromine, such a process is not an industrially practicable process.

The present invention is accomplished under the above-mentioned circumstances, and an object of the invention is to provide a profitable process for isolating effectively i-brassicasterol in a pure state which is useful as an intermediate in the production of brassinolide-related compounds showing an activity on plants, from a mixture of i-sterols derived from a mixture of natural sterols including brassicasterol.

SUMMARY OF THE INVENTION

In an aspect of the present invention, there is provided a process for producing i-brassicasterol, comprising charging a mixture of i-sterols derived from a mixture of sterols including brassicasterol into a column packed with a filler obtained by chemically binding alkyl group(s) of 15 to 24 carbon atoms to silica, and subjecting said mixture of i-sterols to reversed-phase partition column-chromatography while using (i) an alcohol of one to three carbon atoms or a mixture thereof, or (ii) a mixed solvent comprising more than 50% by volume of said alcohol(s) and a solvent other than said alcohol(s) as an eluent, thereby isolating and purifying i-brassicasterol.

BRIEF EXPLANATION OF DRAWINGS

Of the attached drawings.

DETAILED DESCRIPTION OF THE INVENTION

Figure 1:
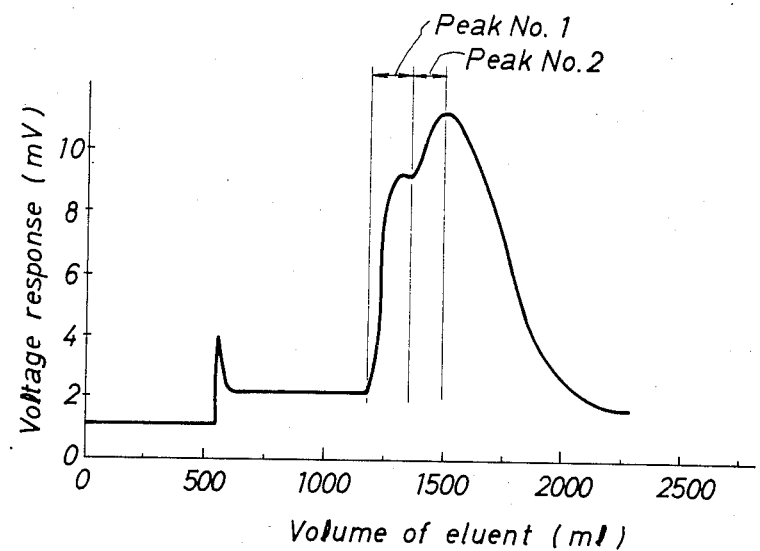
FIGS. 1 to 6 represent respectively the state of elution and separation of i-brassicasterol in the respective chromatograms of Examples 1 to 6, wherein the amount of each i-sterol eluted is shown as the voltage response in the detector.

The characteristic feature of the present invention lies in that a mixture of i-sterols derived from a mixture of sterols including brassicasterol is charged into a column packed with a filler for a reversed-phase partition column chromatography which has been prepared by bonding alkyl groups having 15 to 24 carbon atoms to silica, thereby subjecting the mixture of i-sterols to reversed-phase partition column chromatography while using an alcohol of one to three carbon atoms, a mixture thereof or a mixed solvent containing these alcohols as the main component as an eluent to isolate and purify 3,5-cycloergost-22-en-6β-ol represented by the formula (I).

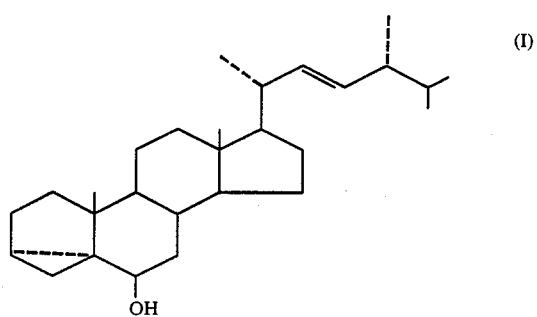

In addition, the present invention has a characteristic feature also in that the mixture of sterols as the starting material, containing brassicasterol is reacted with alkylsulfonyl halide or arylsulfonyl halide to obtain an ester of sulfonic acid and the thus obtained ester of sulfonic acid is hydrolyzed to convert into a mixture of i-sterols, and by subjecting the thus obtained mixture of i-sterols to the reversed-phase partition chromatography, the preparation of i-brassicasterol can be remarkably simplified.

Brassicasterol which is used as the starting material for producing i-brassicasterol in the present invention is present in oils and fats of various animals and plants together with other sterols. As the animal and plant, for instance, *Brassica rapa* L. *var nippoleifera*, *Carthamus tinctorius* L., etc. as plants, and mollusks, particularly shellfishes as animals may be mentioned.

Accordingly, in the present invention, the mixture of sterols as the starting material for i-brassicasterol is prepared by subjecting the above-mentioned oils and fats of animals and plants to a suitable means such as extraction, steam-distillation, etc., thereby removing the components which do not contain sterols and obtaining a mixture of sterols with a content of sterol as high as possible, preferably of higher than 70%, more preferably higher than 80% by weight. In this connection, in the case where the above-mentioned oils and fats of animal or plant are purified and processed to be used for food, the distillate exhausted from a vacuum-steam distillation tower for deodoration or the distillation residue from the distillation tower for fatty acid is rich in sterols and also in brassicasterol. Accordingly, such an exhausted distillate and residue is suitable as the starting material of i-brassicasterol.

In addition, in the case of using such a distillate or residue as the starting material, it is preferable to saponify the starting material by an aqueous methanolic solution of a caustic alkali such as potassium hydroxide and to use only the unsapohifiable material obtained by extracting the saponification mixture with a hydrophobic solvent such as hexane and ethyl ether. More preferably, the mixture of crude sterols obtained as the unsaponifiable material is recrystallized from methanol or petroleum ether to remove the unsaponifiable material other than sterols, and the thus purified unsaponifiable material is used. By subjecting the raw material to such a treatment, for instance, a mixture of sterols having a sterols content of higher than 90% by weight wherein a brassicasterol content in the mixture of sterols is from 9 to 25% by weight, is obtained from the distillate exhausted from the deodorizing vacuum steam distillation tower in the case of purification of rapeseed oil. It is particularly desirable to have raised the concentration of sterols in the mixture of sterols used as the starting material as shown above for improving the efficiency in reaction, isolation and purification.

In the present invention, the mixture of sterols is converted into a form of sulfonic ester by alkylsulfonyl halide or arylsulfonyl halide, for instance, p-toluenesulfonyl chloride or methanesulfonyl chloride in the presence of a tertiary amine, and the substance in a form of sulfonic ester is isolated and hydrolyzed, or hydrolyzed without isolation to obtain a mixture of i-sterols. In this case, hydrolysis is preferably carried out in the presence of a salt or a base having a buffer action to obtain the mixture of i-sterols in a desirable yield. As such a salt, potassium acetate may be exemplified, and as such a base, pyridine may be exemplified.

In the present invention, the thus obtained mixture of i-sterols is directly, or after removing the non-reacted sterols of the raw material by the regular-phase column chromatography while using alumina or silicagel, charged into a reversed-phase partition column packed with a filler prepared by chemically binding alkyl groups to silica and subjected to reversed-phase partition column chromatography while using an alcohol of one to three carbon atoms, mixture thereof or a solvent mixture containing more than 50% by volume of the alcohol as an eluent, thereby eluting and isolating i-brassicasterol.

As the filler used in the above-mentioned column chromatography, a substance obtained by chemically binding alkyl groups of 15 to 24 carbon atoms to silica is preferable, and a substance obtained by chemically binding octadecyl groups to silica is particularly preferable. In the case where other alkyl group than those mentioned above, for instance, alkyl group of 8 carbon atoms was used, it was found that the capacity thereof to separate i-brassicasterol was considerably poor.

By the way, the above-mentioned filler has been commercially available in the name of BONDAPACK ®C 18 and Lichroprep ® RP-18.

The mixture of i-sterols charged into the column as shown above is eluted by using the above-mentioned eluent. As the eluent used herein, (i) an alcohol having one to three carbon atoms, such as methanol, ethanol, 1-propanol and 2-propanol or a mixture thereof, or (ii) a mixed solvent comprising more than 50% by volume of said alcohol(s) and a solvent(s) such as water and a mixture of water with one or more organic solvent(s) having a parameter of solvent strength ($\epsilon_o$) of 0.4 to 0.7 selected from the group consisting of acetone, tetrahydrofuran, dioxane, chloroform, dichloromethane, methyl ethyl ketone, methyl acetate, dimethylsulfoxide and acetonitrile as the third organic solvent component occupying less than 30% by volume may be mentioned (refer to L. R. Synder, Principle of Adsorption Chromatography, Published by M. Dekker, New York, 1968). The preferable mixing ratio (by volume) of alcohol/water in the mixed solvent is from 100/0 to 100/40, and that of alcohol/water/third component (organic solvent other than alcohol) in the mixed solvent is from 100/0.1/1 to 100/50/30.

As has been described, the present invention makes it possible to advantageously and industrially produce i-brassicasterol which is useful as the intermediate of brassinolide-related compounds having a plant growth-promoting activity by using a relatively easily available mixture of sterols as the starting material and subjecting the mixture of i-sterols derived from the mixture of sterols to reversed-phase partition column chromatography.

The present invention will be explained more in detail while referring to Examples as follows.

EXAMPLE 1

Preparation of a mixture of sterols as the starting material

After saponifying the distillate, exhausted from the vacuum steam deodorising distilling tower and obtained as a by-product in the case of purifying rapeseed oil, by an aqueous methanolic solution of potassium hydroxide while following a conventional method, an unsaponifiable material is extracted from the reaction mixture with n-hexane and the residue obtained by distilling off n-hexane from the extract is recrystallized from petroleum ether to obtain a mixture of sterols of a composition of 21.4% by weight of brassicasterol, 32.2% by weight of campesterol and 46.3% by weight of sitosterol.

Tosylation of the mixture of sterols

To a solution of 20 g of the thus obtained mixture of sterols in 200 ml of pyridine, 18 g of p-toluenesulfonyl chloride were added, and the mixture was stirred overnight at a room temperature. After the reaction was over, the reaction mixture was poured into 2 liters of iced water to form crystals, and after collecting the crystals by filtration, the crystals were dried under a reduced pressure to obtain 28.3 g of crude crystals of the tosylate of mixture of sterols, (melting point: 101° to 108° C. after recrystallization from ligroin and NMR: $\delta = 2.50$ (s. p-$\underline{CH_3}$).

Preparation of a mixture of i-sterols

Into 500 ml of acetone, the thus obtained 28.3 g of tosylate were dissolved and an aqueous solution of 31 g of potassium acetate in 140 ml of water was added to the acetone solution to form crystals. After dissolving the crystals in the mother liquor by warming and stirring thereof under a reflux condenser, and subjecting the solution to reflux for 5 hours, the solution was cooled to a room temperature, and the aqueous layer was separated from the organic solvent layer while using a separating funnel. The aqueous layer was washed with 500 ml of petroleum ether, and the washing was mixed with the organic solvent layer. The thus obtained mixture was washed with a saturated aqueous solution of sodium chloride, dehydrated by adding anhydrous sodium sulfate and evaporated to dryness to obtain 19.7 g of a syrup. After adding 100 ml of methanol to the syrup and removing the insoluble matter by filtration of the thus obtained solution, methanol was distilled off from the solution to obtain 16.7 g of a mixture of crude i-sterols showing the following NMR and IR spectrums:

$^1$H-NMR(in CDCl$_3$): $\delta = 5.2$ (m, 22-$\underline{H}$ and 23-$\underline{H}$ of i-brassicasterol), 3.25 (m, 6-$\underline{H}$), 0.2 to 0.6 (m, $\underline{H}$'s of cyclopropane ring).

IR(cm$^{-1}$): 3400, 2940, 2550, 1450, 1370 and 1015.

Isolation and purification of i-brassicasterol

A part (12.3 g) of the mixture of crude i-sterols was subjected to isolation and purification by reversed-phase partition column chromatography under the following conditions.

Column: Bondapack ® C$_{18}$ (diameter of particles of 37 to 50 micrometers, Waters Associates) was packed in a glass column resistant to medium-pressure of 40 mm in diameter and 500 mm in height.
Eluent: a mixture of 100 parts by volume of methanol and 2.5 parts of water,
Pressure of introducing the eluent: 1.0 kg/cm$^2$
Flow rate of the eluent: 18 ml/min
Detector: Shodex ® RI SE -12 (made by Showa-denko Co., Ltd.)
Recorder: 2-Channel recorder REC-2 (made by Pharmacia Fine Chem.).

Figure 2:
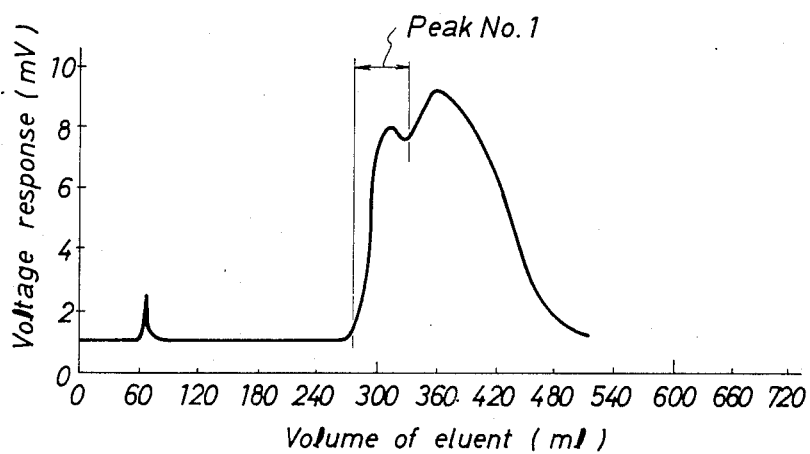

The thus isolated and purified i-brassicasterol was examined by an HPLC (High Pressure-Liquid Chromatography) connected to a high-sensitivity differential refractometer, Shodex ® RI SE-51, and as a result, it was found that 1.9 g of i-brassicasterol of a purity of 90% were obtained from the fraction No. 1 shown in FIG. 1 and 2.1 g of i-brassicasterol of purity of 16% were obtained from the fraction No. 2 shown in FIG. 1 to show the possibility of availability of gram-level amount of i-brassicasterol.

The fraction No. 1 was purified by again subjecting to the same column chromatography to obtain 136 mg of i-brassicasterol of an authentic specimen for analysis as colourless acicular crystals with the following properties:

Melting point: 116° to 118° C. (after recryst. from acetonitrile)

$^1$H NMR (in CDCl$_3$): $\delta = 3.27$ (1H, t, 6-H), 5.18 to 5.22 (2H, m, 22-H and 23-H).

Elementary analytical data: Found: C 84.1% and H 4.0%, Calcd. as C$_{28}$H$_{46}$O: C 84.36% and H 4.01%.

EXAMPLE 2

Preparation of a mixture of i-sterols

Into a solution prepared by dissolving 2.0 g of a mixture of sterols consisting of 15.6% by weight of brassicasterol, 46.1% by weight of campesterol and 38.3% by weight of sitosterol, prepared by the same procedures as in Example 1 in 25 ml of pyridine, 1.0 ml of mesyl chloride was added dropwise, and the mixture was stirred overnight at a room temperature. After adding a solution of 10 ml of water in 100 ml of acetone to the reaction mixture, the mixture was refluxed for 3 hours, and the reaction mixture was condensed to about 50% in volume, and after adding 10 ml of water and 50 ml of petroleum ether to the condensate, the whole matter was shaken, and after an aqueous layer was separated from an organic solvent layer the aqueous layer was washed with 50 ml of petroleum ether and the washing is added to the organic solvent layer, and the combined organic solvent layer was washed with diluted hydrochloric acid, an aqueous solution of sodium hydrogen carbonate and an aqueous saturated solution of sodium chloride in the order, and dehydrated by adding anhydrous sodium sulfate.

By distilling off the solvent from the dehydrated solvent layer 2.0 g of syrup was obtained, and 20 ml of methanol were added to the syrup and the mixture was filtered to remove the insoluble material from the methanolic mixture. By distilling off methanol from the filtrate, 1.57 g of a mixture of crude i-sterols were obtained. (The methanol-insoluble material was sterols in the starting material).

The NMR and IR data of the thus obtained mixture of i-sterols were as follows.

$^1$H-NMR data (in CDCl$_3$): $\delta = 5.2$ (m, 22-H and 23-H of i-brassicasterol), 3.25 (m, 6-H) and 0.2 to 0.6 (m, H's of cyclopropane ring).

IR spectrum (cm$^{-1}$): 3400, 2940, 2850, 1450, 1370 and 1015.

Isolation and purification of i-brassicasterol

A part of the thus obtained mixture of crude i-sterols was subjected to isolation and purification under the following conditions by reversed-phase partition column chromatography.

Amount of the mixture of crude i-sterols: 920 mg,
Column: Lichroprep ® RP-18 packed in a glass tube of 25 mm in diameter and 310 mm in height, (made by E. Merck Co.),
Eluent: methanol
Pressure of introducing the eluent: 1.2 kg/cm$^2$
Flow rate of the eluent: 5.8 ml/min,
Detector: the same as in Example 1
Recorder: the same as in Example 1

The purity of the thus isolated and purified i-brassicasterol was examined by the same procedures as in Example 1, and the result is shown in FIG. 2. From Fraction No. 1 shown in FIG. 2, 148.9 mg of i-brassicasterol of a purity of 92% were obtained.

EXAMPLE 3

From a mixture of sterols comprising 7.8% by weight of brassicasterol, 40.3% by weight of campesterol, 49.8% by weight of sitosterol and 2.1% by weight of stigmasterol, a mixture of crude i-sterols was obtained by the same procedures as in Example 1, and 950 mg of the mixture was subjected to isolation and purification by reversed-phase partition column chromatography under the following conditions.
Column: Lichroprep ® RP-18 packed in a glass tube of 25 mm in diameter and 310 mm in height (made by Merck Co.),
Eluent: a mixture of 100 parts by volume of methanol and 5 parts by volume of water,
Pressure of introducing the eluent: 1.5 kg/cm$^2$,
Flow rate of eluent: 3.2 ml/min,
Detector: Shodex ® RI SE-12 (made by Showa Denko Co., Ltd.) and
Recorder: 2-channel recorder REC-2 (made by Pharmacia Fine Chemicals).

Figure 3:
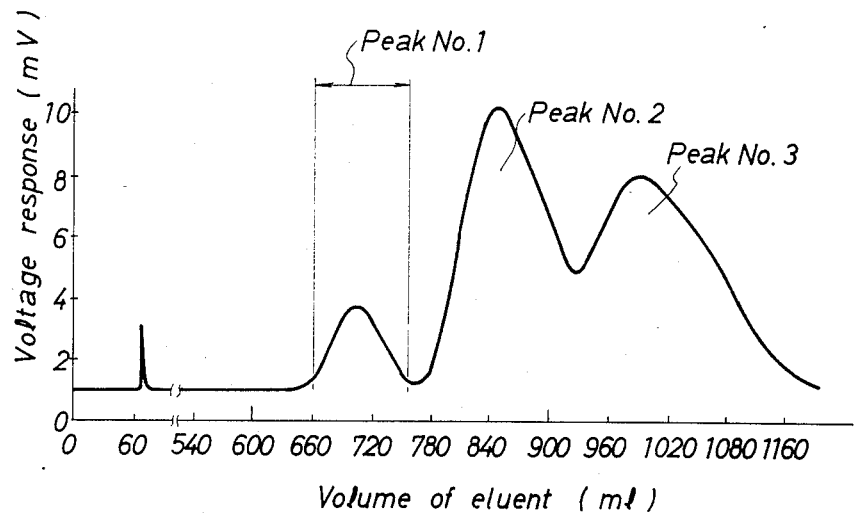

The purity of i-brassicasterol isolated and purified as shown above was analyzed by the same procedures as in Example 1 and the result is shown in FIG. 3.

From the fraction No. 1 shown in FIG. 3, 72.0 mg of i-brassicasterol of a purity of higher than 99% were obtained. In FIG. 3, Peak No. 2 is due to i-campesterol and i-stigmasterol, and Peak No. 3 is due to i-sitosterol and sterols as the starting material. In addition, it was found that even if the content of brassicasterol was small in the sterols as the starting material, i-brassicasterol could be favorably isolated by this procedure.

EXAMPLE 4

From a mixture of sterols comprising 15.6% by weight of brassicasterol, 36.7% by weight of campesterol and 47.7% by weight of sitosterol, a mixture of crude i-sterols was obtained and by using the thus obtained mixture of crude i-sterols, i-brassicasterol was isolated and purified by the same procedures as in Example 1 under the following conditions:
Amount of the mixture of crude i-sterols: 901 mg,
Column: the same as in Example 3,
Eluent: a mixture of methanol, 2-propanol and water of a ratio of 100:50:15 in the order,
Pressure of introducing the eluent: 1.8 kg/cm$^2$,
Flow rate of eluent: 3.0 ml/min,
Detector and Recorder: the same as in Example 3.

Figure 4:
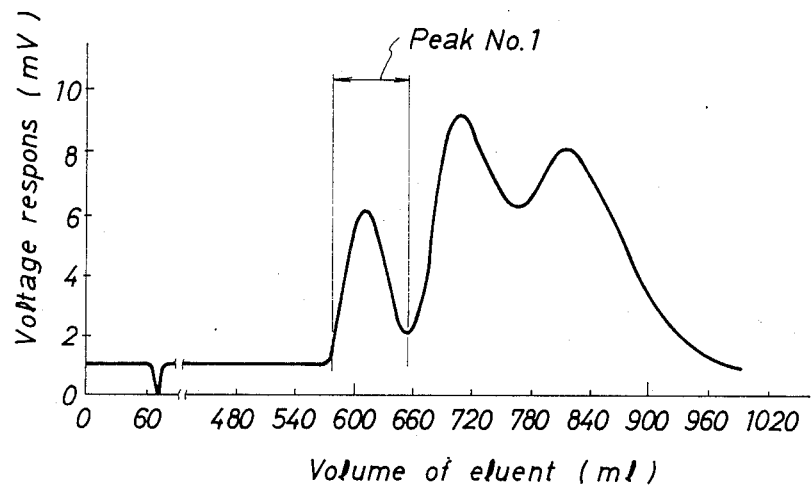

A chromatogram of the thus obtained i-brassicasterol is shown in FIG. 4. From the fraction No. 1 shown in FIG. 4, 137 mg of i-brassicasterol of a purity of higher than 99% were obtained. Namely, it is found that the above-mentioned 3-components eluent comprising methanol, 2-propanol and water can be also applied in the isolation of i-brassicasterol.

EXAMPLE 5

From a mixture of crude i-sterols obtained from a mixture of sterols of a composition of 15.6% by weight of brassicasterol, 36.7% by weight of campesterol and 47.7% by weight of sitosterol, i-brassicasterol was isolated and purified by the same procedures as in Example 1 under the following conditions:
Amount of the mixture of crude i-sterols: 10.0 g
Column: Bondapack ® C$_{18}$ (diameter of particles in the range of 37 to 50 micrometers, Waters Associates) packed in a glass tube of 40 mm in diameter and 500 mm in length resistant to medium pressure),
Eluent: a mixture of 100 parts by volume of methanol, 100 parts by volume of ethanol and 20 parts by volume of water,
Pressure of introducing the eluent: 1.5 kg/cm$^2$,
Flow rate of eluent: 15 ml/min,
Detector and Recorder were the same as in Example 4.

Figure 5:
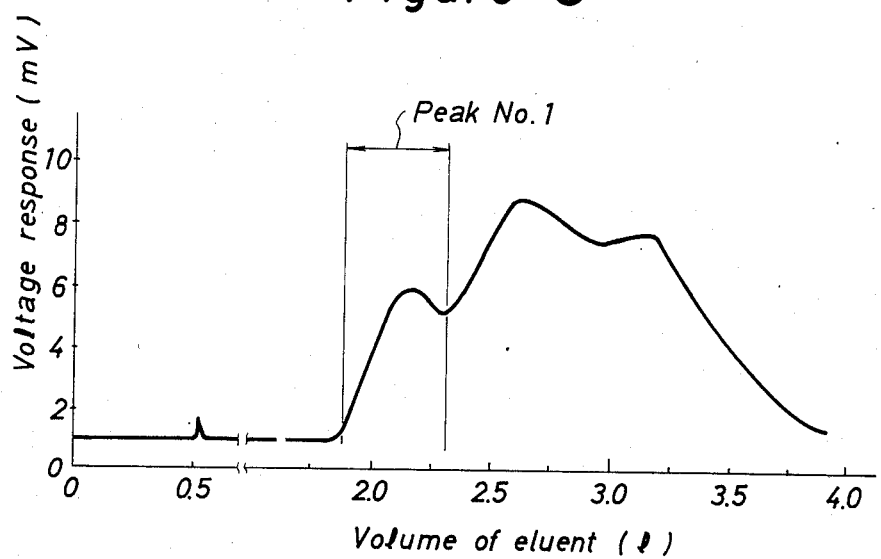

The result of analyzing the thus obtained i-brassicasterol is shown in FIG. 5. From the fraction No. 1 shown in FIG. 5, 1.4 g of i-brassicasterol of a purity of 93% were obtained. From Example 5, it is understandable that the 3-components eluent comprising methanol, ethanol and water is effective in isolation and purification of i-brassicasterol.

EXAMPLE 6

From 9.8 g of the same mixture of crude i-sterol as in Example 5, i-brassicasterol was isolated and purified in the same procedures as in Example 5 under the following conditions:
Column: the same as in Example 5,
Eluent: a mixture of 100 parts by volume of methanol, 10 parts by volume of acetone and 5 parts by volume of water,
Pressure of introducing the eluent: 1.0 kg/cm$^2$,
Flow rate of eluent: 16 ml/min,
Detector and Recorder were the same as in Example 5.

Figure 6:
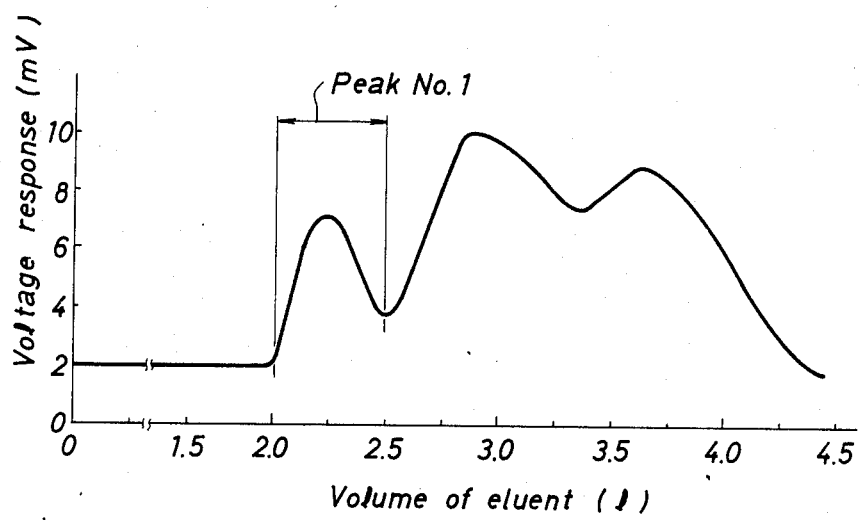

The result of an analysis of the thus obtained i-brassicasterol is shown in FIG. 6. From the fraction No. 1 shown in FIG. 6, 1.4 g of i-brassicasterol of a purity of 95% were obtained. In Example 6, as the representative one of the solvents having a parameter of solvent strength ($\epsilon_o$) in the range of from 0.4 to 0.7, acetone ($\epsilon_o=0.56$) was selected and used, thereby, the object substance was obtained in a high purity.

What is claimed is:

1. A process for producing i-brassicasterol, comprising charging a mixture of i-sterols dervies from a mixture of sterols including brassicasterol into a column packed with a filler obtained by chemically binding alkyl group(s) of 15 to 24 carbon atoms to silica, and subjecting said mixture of i-sterols to reversed-phase partition column-chromatography while using (i) an alcohol of one to three carbon atoms or a mixture thereof, (ii) a mixed solvent comprising more than 50% by volume of said alcohol(s) and less than 50% by volume of water, or (iii) a mixed solvent comprising more than 50% by volume of said alcohol(s) and less than 50% by volume of a mixture of water and organic solvent(s) having a parameter of solvent strength ($\epsilon_o$) of 0.4 to 0.7 selected from the group consisting of acetone, tetrahydrofuran, dioxane, chloroform, dichloromethane, methyl ethyl ketone, ethyl acetate, methyl acetate, dimethylsulfoxide, acetonitrile and a mixture thereof, as an eluent, thereby isolating and purifiying i-brassicasterol.

2. A process according to claim 1, wherein said mixture of sterols including brassicaterol is an unsaponifiable material obtained from a distillate from natural oils and fats in the step of deodorization thereof or a distillation residue of distillation of fatty acids.

3. A process according to claim 1, wherein said mixture of i-sterols is obtained by converting said mixture of sterols including brassicaterol into an ester of sulfonic acid with alkylsulfonyl halide or arylsulfonyl halide, and hydrolyzing the thus obtained ester of sulfonic acid.

* * * * *